United States Patent [19]
Wagner

[11] Patent Number: 5,334,203
[45] Date of Patent: Aug. 2, 1994

[54] SPINAL FIXATION SYSTEM AND METHODS

[75] Inventor: Erik J. Wagner, Allen, Tex.

[73] Assignee: AMEI Technologies Inc., Wilmington, Del.

[21] Appl. No.: 954,561

[22] Filed: Sep. 30, 1992

[51] Int. Cl.⁵ .................... A61B 17/58; B25G 3/00; A44B 1/04
[52] U.S. Cl. ........................ 606/61; 606/103; 606/69; 606/53; 403/236; 403/233; 403/396; 24/397
[58] Field of Search ............. 606/53, 54, 60, 61, 606/69, 86, 103-105; 403/236, 233, 396; 24/590, 597; 411/400; 248/230, 222.3

[56] References Cited

U.S. PATENT DOCUMENTS

| | | | |
|---|---|---|---|
| 427,642 | 5/1890 | Wack | 411/400 X |
| 1,849,999 | 3/1932 | Birkenmaier | 403/396 X |
| 3,052,868 | 9/1962 | Margolies | 403/396 X |
| 3,693,616 | 9/1972 | Roaf et al. | 606/61 |
| 4,003,376 | 1/1977 | McKay et al. | 606/61 |
| 4,361,141 | 11/1982 | Tanner | 128/69 |
| 4,611,582 | 9/1986 | Duff | 128/69 |
| 4,771,767 | 9/1988 | Steffee | 606/61 X |
| 4,790,297 | 12/1988 | Luque | 128/69 |
| 4,913,134 | 4/1990 | Luque | 128/69 |
| 5,002,542 | 3/1991 | Frigg | 606/61 |
| 5,005,562 | 4/1991 | Cotrel | 128/69 |
| 5,007,909 | 4/1991 | Rogozinski | 606/61 |
| 5,041,113 | 8/1991 | Biedermann et al. | 606/61 |
| 5,074,864 | 12/1991 | Cozad et al. | 606/54 |
| 5,084,049 | 1/1992 | Asher et al. | 606/61 |
| 5,092,893 | 3/1992 | Smith | 606/61 X |
| 5,102,412 | 4/1992 | Rogozinski | 606/61 |
| 5,108,395 | 4/1992 | Laurain | 606/61 |
| 5,129,899 | 7/1992 | Small et al. | 606/61 |
| 5,147,360 | 9/1992 | Dubousset | 606/61 |
| 5,180,381 | 1/1993 | Aust et al. | 600/61 |
| 5,190,545 | 3/1993 | Corsi et al. | 606/60 X |

FOREIGN PATENT DOCUMENTS

| | | | |
|---|---|---|---|
| 0446092 | 9/1991 | European Pat. Off. | 606/61 |
| 3839859 | 8/1989 | Fed. Rep. of Germany | 606/86 |
| 2254304 | 7/1975 | France | 606/61 |
| 2645427 | 10/1990 | France | 606/61 |
| 825042 | 5/1981 | U.S.S.R. | 606/61 |

OTHER PUBLICATIONS

Danek Surgical Technique Manual, "TSRH ™ Crosslink ™", Danek Medical, Inc., pp. 1-8.

Primary Examiner—Robert A. Hafer
Assistant Examiner—Brian F. Hanlon
Attorney, Agent, or Firm—Baker & Botts

[57] ABSTRACT

A system and method to form a medical construct using surgical rods and connectors. A pair of surgical rods such as those used in fusing vertebrae of the spine are attached to each other with connectors to form a medical construct. The connector includes a plate with a pair of double hook bolts which are attached to the rods. The double hook bolts and rods may be used to provide a rigid or semi-rigid medical construct depending upon the attachment of the double hook bolts with the plate. The connector is assembled prior to the surgical procedure and eliminates any need for manipulating small washers, screws and bolts during installation of the medical apparatus within a patient.

15 Claims, 2 Drawing Sheets

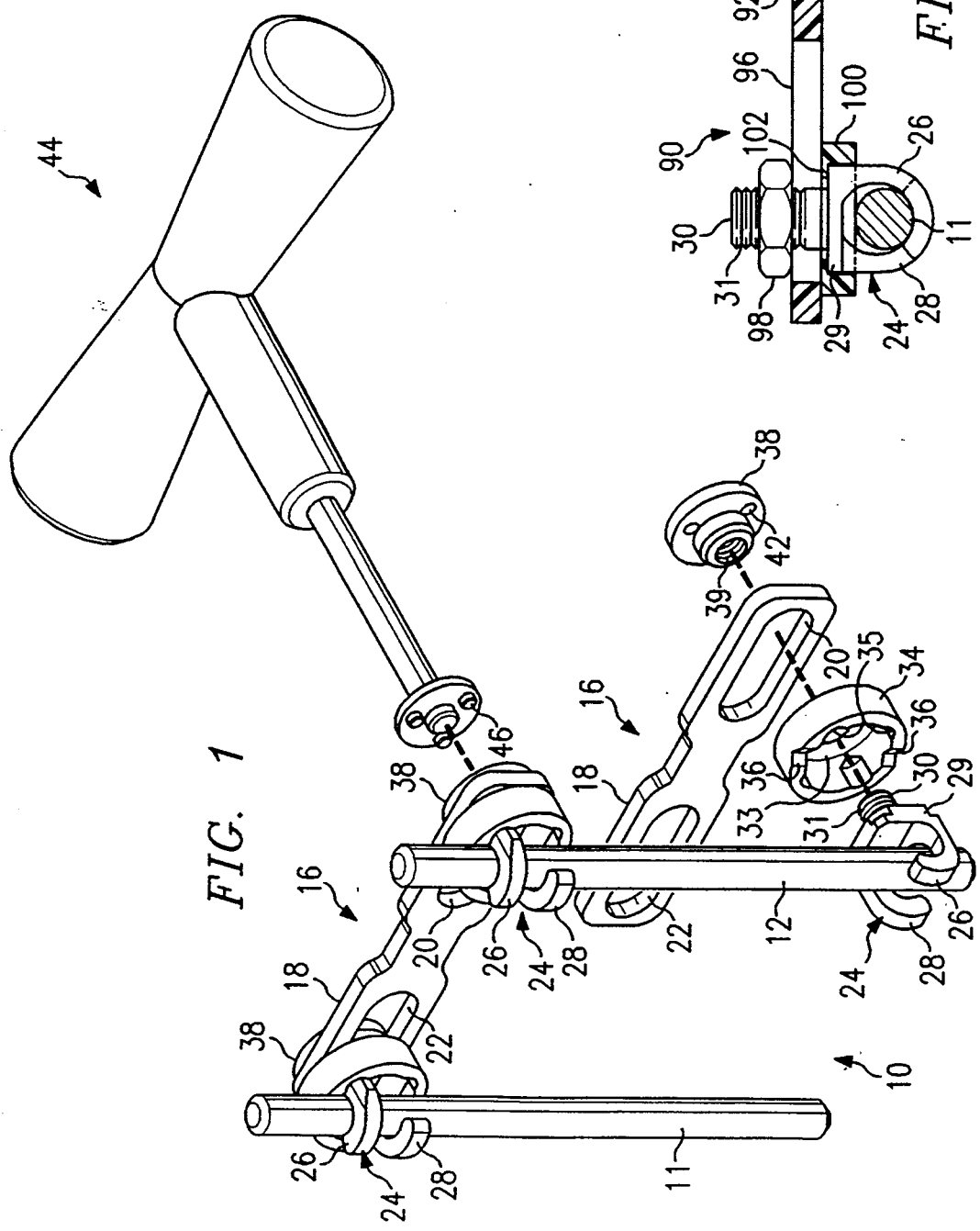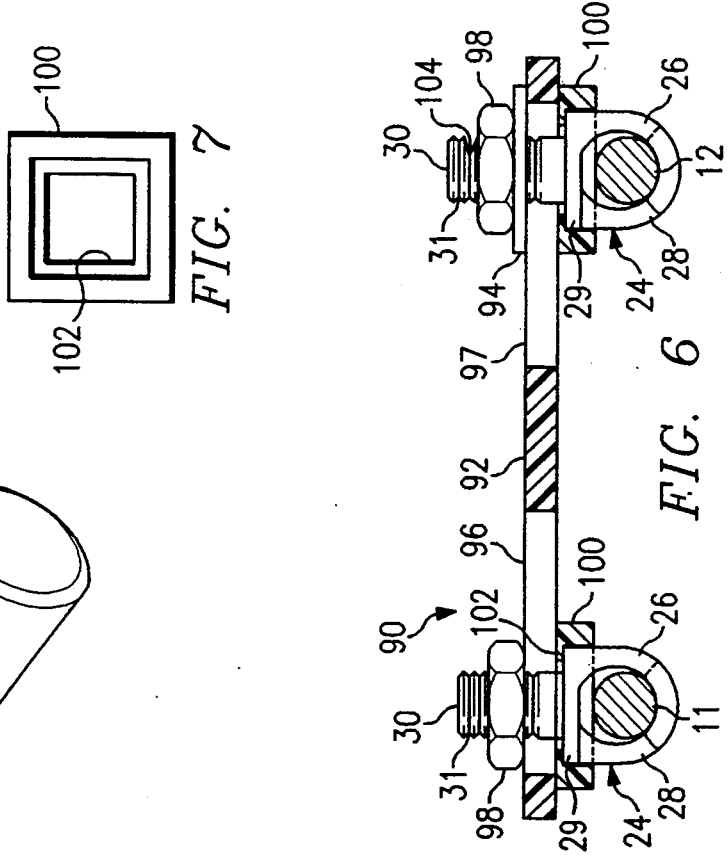

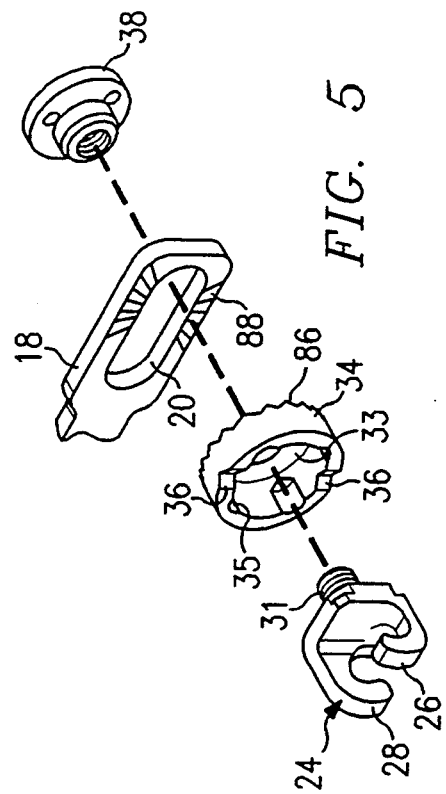
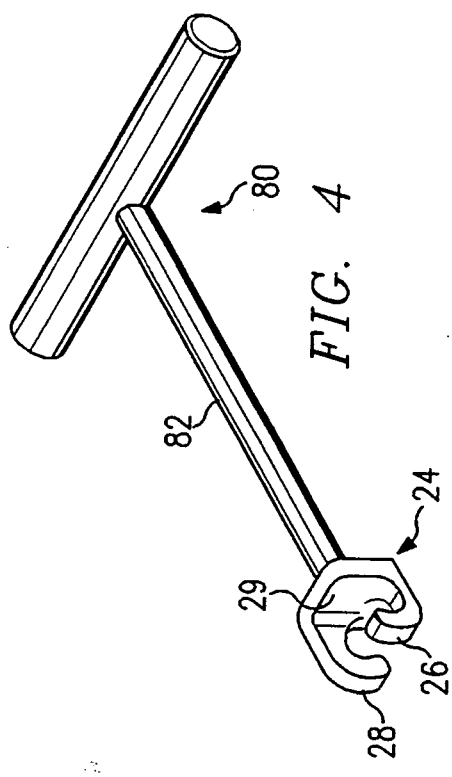
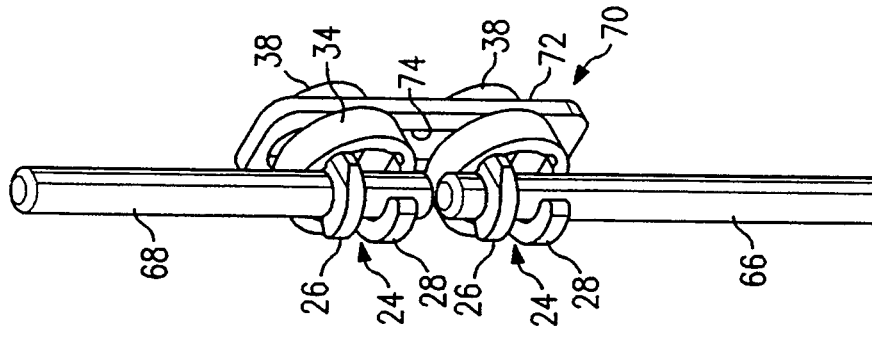
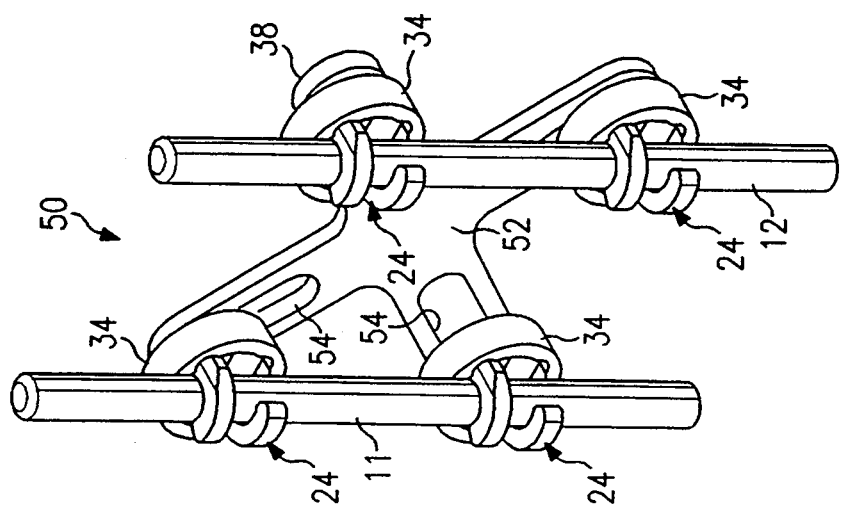

SPINAL FIXATION SYSTEM AND METHODS

TECHNICAL FIELD OF THE INVENTION

This invention relates to surgical tools and medical constructs, and more particularly relates to connectors used with rods associated with spinal fixation and correction of spinal curves.

BACKGROUND OF THE INVENTION

Spinal interlaminar fixation including lumbosacral fusion and correcting scoliotic curves are well known and frequently used medical procedures. Spinal fixation systems, frequently used to correct problems in the lumbar, are installed on opposite sides of the sacrum adjacent to the lumbosacral junction. Such systems often include a pair of rods which are placed on opposite sides of the portion of the spine which is intended to be fused. Pedicle, lateral and oblique mounting means may be used to secure the rods relative to the desired portion of the spine which will be fused by the fixation system.

Crosslinking of spinal instrumentation or spinal rods is designed to prevent rod migration and to increase stiffness of the surgical construct. Even with rigid crosslinking, all spinal constructs are designed to provide only temporary fixation until solid bone fusion has been completed. Without adequate bone fusion, fatigue endurance of the construct will be exceeded, which may cause rod fracture.

Various connectors and cross-links have been used to attach spinal rods to each other when the rods have been installed at the desired location adjacent to the patient's spine. Examples of such spinal fixation systems and related equipment are shown in U.S. Pat. Nos. 4,790,297 and 4,913,134 issued to Eduardo R. Luque. Many of the presently available spinal fixation systems require placing extra hardware such as eyebolts on the spinal rods before attaching the rod to pedicle screws or hooks at selected locations along the patient's spine. Also, presently available fixation systems require careful alignment of the hardware used to connect the spinal rods with each other.

A need has thus arisen for improved connectors to attach spinal rods to each other without requiring additional manipulation of the rods or placing the rods in a specific geometric relationship with respect to each other, and at the same time reducing requirements to assemble small pieces of hardware during the surgical procedure.

SUMMARY OF THE INVENTION

In accordance with the present invention, the advantages and problems associated with previous connectors used with spinal rods have been substantially reduced or eliminated. The present invention allows a surgeon to install connectors between spinal rods without having to position the rods at a specific distance relative to each other and without having to install additional hardware on the rods prior to implanting the rods in a patient. Connectors of the present system can be used with rods having different diameters and arranged with different spacial relationships relative to each other.

Connectors of the present system may be used to join rods which are parallel to each other, offset from each other, converge or diverge at angles relative to each other, or are aligned end to end. Connectors of the present invention increase the stability of bilateral posterior fixation rods associated with spinal fusion. The connectors may be attached after the rods have been secured to selected portions of the spine. Connectors of the present invention may also be used to extend existing implants or medical constructs by adding additional rod sections and to repair broken rods.

Connectors of the present invention may be attached to spinal rods during revision surgery without requiring disassembly or modification of the spinal rods and associated construct attached to the patient's spine. Connectors of the present invention can accommodate rods having different diameters and variations between the spacing and orientation of the rods.

A significant technical advantage of the present invention is that the connector is installed as a fully assembled unit during the surgical procedure. Assembly of individual components and small pieces of hardware is not required as part of the surgical procedure.

BRIEF DESCRIPTION OF THE DRAWINGS

For a more complete understanding of the present invention, and the advantages thereof, reference is now made to the following descriptions taken in conjunction with the accompanying drawings, in which:

FIG. 1 is an isometric pictorial with portions broken away and other portions exploded showing a spinal fixation system incorporating the present invention;

FIG. 2 is an isometric pictorial showing an alternative configuration for a connector incorporating the present invention;

FIG. 3 is an isometric pictorial showing an alternative connector of the present invention attaching two rods longitudinally;

FIG. 4 is a perspective view of a surgical wrench incorporating the present invention;

FIG. 5 is an enlarged isometric drawing with portions broken away showing a connector of the present invention modified to limit rotation;

FIG. 6 is a drawing in elevation and section with portions broken away showing an alternative embodiment of the present invention; and FIG. 7 is a plan view of a spacer for use with the connector shown in FIG. 6.

DETAILED DESCRIPTION OF THE INVENTION

The preferred embodiments of the present invention and its advantages are best understood by referring to FIGS. 1 through 7 of the drawings, like numerals being used for like and corresponding parts of the various drawings.

Spinal fixation or fusion system 10 incorporating the present invention is shown in FIG. 1. Fixation system 10 includes rods 11 and 12 which are designed to be placed bilaterally on either side of a patient's spine (not shown) to assist in fusing vertebrae (not shown) disposed between rods 11 and 12. Pedicle screws (not shown) or hooks (not shown) may be used to secure rods 11 and 12 to selected portions of the patient's spine. An important element in spinal fixation system 10 is to include one or more cross-links or connectors 16 between rods 11 and 12. Using connectors 16 results in a surgical construct with improved rigidity that enhances fusion of the vertebrae disposed between rods 11 and 12.

For spinal fixation system 10, two connectors 16 are shown. Depending upon the specific medical procedure and design requirements for rods 11 and 12, one connector 16 or multiple connectors 16 may be used to join rods 11 and 12 to form the desired medical construct.

The various components and subassemblies which comprise connector 16 are secured to or carried by plate 18. Plate 18 has the general configuration of an elongated rectangle with longitudinal slots 20 and 22 formed near each end of plate 18. As will be explained later in more detail, plate 18 with slots 20 and 22 provide substantial flexibility in the use and installation of connector 16 during various medical procedures. The components and subassemblies which comprise connector 16 and other connectors 50, 70, and 90 of the present invention are manufactured from biocompatible material such as stainless steel or titanium.

Double hook bolts 24 are slidably disposed within slots 20 and 22 respectively. Each double hook bolt 24 includes a pair of hooks 26 and 28 which extend from one side of collar 29 and are sized to fit securely around and engage with rods 11 and 12. Threaded stem 30 projects from the other side of collar 29 through slots 20 and 22 respectively. Spacer 34 is disposed between hook bolt collar 29 and plate 18. Collar 29 is sized to fit within spacer 34 against shoulder 33. Four grooves 35 are formed within spacer 34 to receive square collar 29 therein. Grooves 35 and square collar 29 cooperate to prevent rotation of double hook bolt 24 relative to spacer 34 after connector 16 has been assembled. Shoulder 33 prevents spacer 34 from sliding over collar 29 prior to engaging connector 16 with rods 11 and 12.

Spacer 34 preferably has a pair of notches 36 which are sized to engage a portion of the outside diameter of rods 11 and 12. Each spanner nut 38 with internal threads 39 is used to engage external threads 31 on stem 30 and secure its associated double hook bolt 24 to plate 18 with its associated spacer 34 between rods 11 and 12 and plate 18. Spacer 34 cooperates with threads 31 and 39 to allow double hook bolts 24 to securely attach connector 16 to rods 11 and 12.

An important advantage of the present invention is that connector 16 and all of its associated components and subassemblies can be fully assembled prior to beginning the surgical procedure. It is not necessary to place double hook bolts 24 or other components of connector 16 on rods 11 and 12 prior to installing rods 11 and 12 at the desired location on the patient's spine.

Hooks 26 and 28 are spaced from each other with a sufficient gap to allow the outside diameter of rods 11 and 12 to be inserted therebetween. The orientation of hooks 26 and 28 is selected to correspond with threads 31 on stem 30 and threads 39 in spanner nut 38. As spanner nut 38 is tightened onto stem 30, double hook bolt 24 will rotate so that hooks 26 and 28 will engage rod 11 or 12. Spanner nut 38 has a plurality of holes 42 in its outer periphery. Spanner wrench 44 has similar projections 46 which are sized to engage holes 42. Spanner wrench 44 preferably includes torque limiting means such that during the surgical procedure, the torque transmitted from wrench 44 via spanner nut 38 to double hook bolt 24 will be limited to a selected value such as 150 lbs/in.

The present invention allows considerable flexibility in designing connectors to attach rods 11 and 12 with each other. As shown in FIG. 2, connector 50 is formed from cross plate 52 having the general configuration of an X. Slots 54 similar to slots 20 and 22 are formed in each leg of cross plate 52 and one double hook bolt 24 disposed in each slot 54. Connector 50 provides substantial rigidity in securing rods 11 and 12 with each other and may be particularly useful with heavy patients.

During some medical procedures, it may be necessary to repair a rod which has broken. For some spinal conditions it may be necessary to lengthen the initial medical construct as additional vertebrae deteriorate. The present invention may be used to join two rods which are spaced longitudinally with respect to each other for these procedures. Connector 16 could be used for this purpose or the present invention may be modified to provide connector 70 for these medical procedures.

Connector 70 as shown in FIG. 3 includes a rectangular plate 72 which has only one longitudinal slot 74 extending therethrough. A pair of double hook bolts 24 are disposed in slot 74 to longitudinally secure rods 66 and 68 to each other. FIG. 3 shows rods 66 and 68 in coaxial longitudinal alignment. Double hook bolts 24 and connector plate 74 are particularly advantageous for use when the rods are not axially aligned. Slot 74 cooperates with spacer 34 and spanner nut 38 to allow orienting double hook bolts 24 at any angle with respect to each other and slot 74. Therefore, connector 70 may be used to attach rods 66 and 68 which are substantially out of longitudinal alignment with each other. Also, slot 74 allows attaching rod 66 and 68 with substantial variation in the gap between the adjacent ends of each rod 66 and 68. Slots 20 and 22 in plate 18 cooperate with double hook bolts 24 in a similar manner to allow for wide variations in the orientation of rods 11 and 12 with respect to each other and connectors 16.

During medical procedures when spanner wrench 44 is used to tighten spanner nut 38 onto stem 30 of double hook bolt 24, the torque may be transmitted from rod 11 and 12 to the patient. An important advantage of the present invention is the use of wrench 80 with double hook bolt 24 secured to one end. Wrench 80 is shown in FIG. 4 with T shaped handle 82. Various other handle designs could be used for wrench 80. Double hook bolt 24 allows a surgeon to engage rod 12 or 11 with wrench 80 and to counter the torque applied as each spanner nut 38 and its associated double hook bolt 24 are tightened. Thus, wrench 80 prevents transmitting torque through rods 11 and 12 or 66 and 68 to the patient's spine.

As previously noted, the present invention allows substantial flexibility in the orientation of connectors 16 and 70 relative to rods 11 and 12. For some surgical procedures, it may be desired to limit the capability of double hook bolts 24 to rotate relative to plates 18 or 72. FIG. 5 shows the modification of spacer 34 and the periphery of slot 20 to prevent relative rotation between these components. A plurality of serrations 86 and 88 are machined in spacer 34 and plate 18 to prevent rotation therebetween after double hook bolt 24 has been tightened with its associated spanner nut 38. Serrations 86 and 88 also cooperate with each other to prevent longitudinal movement of double hook bolt 24 in slot 20. This same modification may be incorporated into plates 72 and 52 as desired.

The present invention allows selecting various types of bolts and nuts to meet specific design requirements. Connector 90 shown in FIG. 6 includes plate 92 with longitudinal slots 96 and 97 formed therein. Plate 92 may have a configuration similar to plate 18 of connecter 16 or plate 92 may be rectangular, circular, oval shaped, etc. For purposes of illustration, double hook bolt 24 attached to rod 11 is secured within slot 96 by nut 98. Rectangular spacer 100 is disposed between slot 96 and collar 29 on double hook bolt 24. Spacer 100 has a rectangular configuration as shown in FIG. 7. Shoulder 102 on the interior of spacer 100 cooperates with collar 29 to prevent spacer 100 from sliding off of double hook bolt 24 prior to engagement with rods 11 and 12. If desired, notches could be formed in spacer 100 in the same manner as notches 36 are provided in spacer 34.

Alternative design flexibility is shown by double hook bolts 24 which are used to attach rod 12 to connector 90. Washer 94 is disposed between nut 98 and slot 97. Various types of washers, including lock washers, could be used for washer 94. Also, stem 30 may be staked as indicated at 104 to prevent disengagement of nut 98 from double hook bolt 24. Shoulder 33 in spacer 34 and shoulder 102 in spacer 100 are examples of features which allow installing connectors of the present invention as fully assembled units. Again, connector 90 is shown to illustrate the various alternative design configurations which are possible from using the present invention.

The present invention has been described with respect to spinal rods and spinal fixation procedures. Those skilled in the art will readily note additional orthopedic instrumentation and surgical procedures which will benefit from using connectors 16, 50, 70, and 90 and double hook bolts 24 of the present invention.

The present invention has been described with respect to generally elongated rectangular plates and slot means which extend longitudinally through plates 18, 52, 72 and 92 at selected locations. Those skilled in the art will readily appreciate that the present invention may be used with plates of various configurations13 square, circular, oval, etc. Slot means may be formed in the plates longitudinally, radially, or at diverging or converging angles with respect to each other. The slot means may be a single slot 74, a pair of slots 20 and 22 or a plurality of slots 54. The present invention allows using a plate with slot means which are designed to best meet the needs of each patient and each surgical procedure.

Although the present invention and its advantages have been described in detail, it should be understood that various changes, substitutions and alterations can be made therein without departing from the spirit and scope of the invention as defined by the appended claims.

What is claimed is:

1. A connector for use in securing rods to each other during medical procedures comprising:
   a plate with a first elongated slot formed in a first end of said plate;
   a first double hook bolt extending through the first elongated slot for coupling to a first one of the rods, said double hook bolt including a first hook for partially encircling the first rod from a first direction and a second hook for partially encircling the first rod from a second direction opposite from said first direction;
   said first hook oriented in said first direction and said second hook spaced from said first hook and said second hook oriented in a second direction opposite from said first direction; and
   means for securing the first double hook bolt to the plate.

2. The connector of claim 1, further comprising a spacer disposed between a portion of the first double hook bolt and the plate.

3. The connector of claim 2, further comprising:
   a pair of notches formed on the spacer; and
   the notches sized to engage a portion of the exterior of the rods.

4. The connector of claim 2, further comprising means for preventing rotation of the spacer relative to the plate.

5. The connector of claim 4 wherein the means for preventing rotation further comprises:
   serrations formed on the portion of the spacer adjacent to the plate; and
   matching serrations formed on the plate adjacent to the spacer.

6. The connector of claim 1, further comprising:
   a second elongated slot formed in a second end of said plate; and
   a second double hook bolt disposed within the second elongated slot.

7. The connector of claim 1 further comprising:
   a spacer disposed between a portion of the first double hook and the plate;
   the first double hook bolt having a collar with a threaded stem extending in one direction from the collar and the first and second hooks extending in the opposite direction from the collar; and
   the interior of the spacer sized to receive the collar whereby rotation of the first double hook bolt is prevented with respect to the spacer when the collar is disposed therein.

8. The connector of claim 1 further comprising a second double hook bolt extending through the first elongated slot.

9. The method of connecting a pair of rods with each other comprising the steps of:
   forming a plate with an elongated slot means extending there through;
   forming a pair of double hook bolts, each of the bolts with a first hook for partially encircling a rod in a first direction and a second hook for partially encircling the rod from a second direction opposite from the first direction;
   the first hook oriented in the first direction and the second hook spaced from the first hook, and the second hook oriented in the second direction opposite from the first direction;
   securing the first double bolt and the second double hook bolt within the elongated slot means;
   placing the first double hook bolt over the first rod;
   placing the second double hook bolt over the second rod; and
   rotating the first hook bolt and the second hook bolt to securely anchor the plate to the pair of rods.

10. The method of connecting a pair of rods as defined in claim 9 further comprising the steps of:
    forming said plate with a second elongated slot extending therethrough, said first elongated slot formed at a first end of said plate and said second elongated slot formed at a second end of said plate; and
    securing the first double hook bolt in the first elongated slot and securing the second double hook bolt in the second elongated slot.

11. The method of connecting a pair of rods as defined in claim 10 further comprising the steps of:
    placing a spacer between each double hook bolt and its associated elongated slot;
    attaching a nut to a portion of each double hook bolt which extends through its respective elongated slot; and securing each double hook bolt to the plate with its respective nut.

12. A connector for use in securing rods to each other during medical procedures comprising:
    a plate having multiple legs, each of the legs having an end with an elongated slot formed therein;
    a plurality of double hook bolts for coupling to the rods, each bolt extending through a corresponding elongated slot in one of the legs, each bolt including a first hook for partially encircling a rod in a first direction and a second hook for partially encircling the rod from a second direction opposite from the first direction;
    said first hook oriented in said first direction and said second hook spaced from said first hook and oriented in a second direction opposite from said first direction; and
    means for securing each of the double hook bolts to the plate.

13. The connector of claim 12, wherein the plate comprises four legs.

14. A method of connecting a pair of rods with each other comprising the steps of:
    forming a plate having a plurality of legs extending therefrom;
    forming a plurality of elongated slots with one of said elongated slots extending through each of the legs;
    forming a plurality of double hook bolts, each of the bolts with a first hook for partially encircling a rod in a first direction and a second hook for partially encircling the rod from a second direction opposite from the first direction;
    said first hook oriented in said first direction and said second hook spaced from said first hook and said second hook oriented in a second direction opposite from said first direction;
    securing each of the double hook bolts respectively within one of the elongated slots;
    assigning a first number of said bolts to a first set and assigning a second number of said bolts to a second set;
    placing each bolt of the first set over the first rod;
    placing each bolt of the second set over the second rod; and
    rotating each of the bolts to secure the plate to the rods.

15. The method of claim 14 wherein the step of forming the plate comprises the step of:
    forming the plate with four legs extending therefrom; and
    assigning a first pair of the bolts to the first set and a second pair of the bolts to the second set.

* * * * *

UNITED STATES PATENT AND TRADEMARK OFFICE
CERTIFICATE OF CORRECTION

PATENT NO. : 5,334,203
DATED : Aug. 2, 1994
INVENTOR(S) : Wagner

It is certified that error appears in the above-identified patent and that said Letters Patent is hereby corrected as shown below:

Column 6, Claim 9, line 14, after "first double", insert -- hook --.

Signed and Sealed this

Fifth Day of December, 1995

Attest:

BRUCE LEHMAN

*Attesting Officer*    Commissioner of Patents and Trademarks